(12) United States Patent
Menhardt et al.

(10) Patent No.: US 12,300,363 B2
(45) Date of Patent: May 13, 2025

(54) AUTOMATICALLY GENERATING RULES FOR LAB INSTRUMENTS

(71) Applicant: Beckman Coulter, Inc., Brea, CA (US)

(72) Inventors: Wido Menhardt, Los Gatos, CA (US); Christoph Moellers, Eichenau (DE); Santosh Kookal, Pasadena, CA (US)

(73) Assignee: Beckman Coulter, Inc., Brea, CA (US)

( * ) Notice: Subject to any disclaimer, the term of this patent is extended or adjusted under 35 U.S.C. 154(b) by 1192 days.

(21) Appl. No.: 16/758,325

(22) PCT Filed: Oct. 23, 2018

(86) PCT No.: PCT/US2018/057089
§ 371 (c)(1),
(2) Date: Apr. 22, 2020

(87) PCT Pub. No.: WO2019/083993
PCT Pub. Date: May 2, 2019

(65) Prior Publication Data
US 2020/0342962 A1    Oct. 29, 2020

Related U.S. Application Data

(60) Provisional application No. 62/577,465, filed on Oct. 26, 2017.

(51) Int. Cl.
*G16H 10/40* (2018.01)
*G06N 5/04* (2023.01)

(52) U.S. Cl.
CPC .............. *G16H 10/40* (2018.01); *G06N 5/04* (2013.01)

(58) Field of Classification Search
None
See application file for complete search history.

(56) References Cited

U.S. PATENT DOCUMENTS

| | | | |
|---|---|---|---|
| 8,786,425 B1 * | 7/2014 | Hutz | G08B 23/00 340/541 |
| 2012/0109531 A1 * | 5/2012 | Knafel | G05B 19/41865 702/19 |

FOREIGN PATENT DOCUMENTS

WO    WO-2019083993 A1    5/2019

OTHER PUBLICATIONS

Karthikeyan, T., and N. Ravikumar. "A survey on association rule mining." International Journal of Advanced Research in Computer and Communication Engineering 3, No. 1 (2014): 2278-1021. (Year: 2014).*

(Continued)

*Primary Examiner* — Vincent Gonzales
(74) *Attorney, Agent, or Firm* — FROST BROWN TODD LLP

(57) ABSTRACT

Disclosed herein are methods and systems for automatically generating processing rules to be used for automated decision-making when operating instruments to analyze and process biological samples (e.g., for the presence, absence, or concentration of analytes). For example, some automatically generated processing rules may set forth conditions and criteria in which some test results obtained from the biological samples can be automatically validated and sent out, while other test results are flagged for additional review. The processing rules can be generated based on patterns observed with the actions taken for historical test results associated with similar biological samples.

20 Claims, 7 Drawing Sheets

(56) References Cited

OTHER PUBLICATIONS

Krasowski, Matthew D., Scott R. Davis, Denny Drees, Cory Morris, Jeff Kulhavy, Cheri Crone, Tami Bebber et al. "Autoverification in a core clinical chemistry laboratory at an academic medical center." Journal of pathology informatics 5, No. 1 (2014): 13. (Year: 2014).*
Huck, Amelia, and Kent Lewandrowski. "Utilization management in the clinical laboratory: an introduction and overview of the literature." Clinica Chimica Acta 427 (2014): 111-117. (Year: 2014).*
Sepulveda, Jorge L., and Donald S. Young. "The ideal laboratory information system." Archives of Pathology and Laboratory Medicine 137, No. 8 (2013): 1129-1140. (Year: 2013).*
"International Application Serial No. PCT/US2018/057089, International Search Report mailed Feb. 5, 2019", 2 pgs.
"International Application Serial No. PCT/US2018/057089, Written Opinion mailed Feb. 5, 2019", 8 pgs.
Shih, Mu-Chin, et al., "Building and Validating an Autoverification System in the Clinical Chemistry Laboratory", Laboratory Medicine, vol. 42. No. 11, (Nov. 1, 2011), 668-673.

* cited by examiner

AUTOMATICALLY GENERATING RULES FOR LAB INSTRUMENTS

CROSS-REFERENCES TO RELATED APPLICATIONS

This application is a U.S. National Stage Filing under 35 U.S.C. 371 from International Application No. PCT/US2018/057089, filed on Oct. 23, 2018, and published as WO 2019/083993 on May 2, 2019, which application claims priority to U.S. Provisional Application No. 62/577,465, filed on Oct. 26, 2017, the contents of which are incorporated by reference herein in their entirety.

BACKGROUND

In order to diagnose a disease or evaluate the health of a subject, biological samples will often be collected from the subject for evaluation using one or more instruments. For instance, a laboratory may have an array of different instruments that can be utilized to perform tests on the biological samples. These test results can be further analyzed and processed in order to formulate a diagnosis or to determine that additional testing is required.

In many cases, it is laboratory staff that oversees a biological sample as it progresses through the testing workflow, interprets the accompanying test results, and makes key decisions as to whether additional testing is required. Since these laboratories often test and analyze the biological samples of many subjects at a time, there can be large burdens associated with all the oversight of the laboratory staff needed for testing all of those biological samples.

In order to alleviate this burden, processing rules can be established for automating decisions in the testing workflow. For instance, numerous rules can be established that set forth a set of conditions or criteria under which the test results for a biological sample are automatically verified, such that no additional testing is needed on that biological sample. However, a single laboratory may employ hundreds or thousands of such rules, and having users (e.g., laboratory staff) generate all of these rules may similarly be a tremendous time and knowledge burden.

Thus, there exists a need for ways to make it easier to generate and implement processing rules for use in the testing workflow. This will make it faster to test and evaluate numerous biological samples, improve the accuracy and consistency in any decision making, and reduce the amount of oversight needed.

Embodiments of the present disclosure address these and other challenges, individually and collectively.

BRIEF SUMMARY

Embodiments of methods, systems, and devices described in the present disclosure may be used to automatically generate processing rules to be used when operating instruments to analyze and process biological samples (e.g., for the presence, absence, or concentration of analytes).

One embodiment of the present disclosure is directed to a method comprising: executing a first set of test orders for a first plurality of samples; processing the first plurality of samples to obtain a first plurality of test results; and generating one or more processing rules based at least on input data and the first plurality of test results. In one embodiment the step of generating rules is performed by a computer. The method may also be performed by a sample processing system comprising an information management apparatus comprising a first data processor and a first computer readable medium, and a control system comprising a second data processor, and a second computer readable medium. The method may also comprise: receiving, by the information management apparatus, the first set of test orders for the first plurality of samples; providing, by the information management apparatus, the first set of test orders to the control system; receiving, by the control system, the first plurality of test results from the one or more instruments corresponding to the first set of test orders; providing, by the control system, the first plurality of test results to the information management apparatus; receiving, by the information management apparatus, the input data from the information management apparatus, receiving, by the control system, the input data from the information management apparatus; after generating the one or more processing rules, receiving, by the control system from the information management apparatus, additional test orders for an additional plurality of samples; and after generating the one or more processing rules, executing, by the control system, the additional test orders for the additional plurality of samples, so that the additional plurality of samples are processed on the one or more instruments in communication with the control system according to the one or more generated processing rules.

Another embodiment of the present disclosure is directed to a sample processing system comprising: a data processor; and a computer readable medium, the computer readable comprising code executable by the data processor to perform a method including: executing a first set of test orders for a first plurality of samples; processing the first plurality of samples to obtain a first plurality of test results; and generating one or more processing rules based at least on input data and the first plurality of test results. The sample processing system may also include an information management apparatus comprising a first data processor and a first computer readable medium; and a control system comprising a second data processor, and a second computer readable medium, the control system communicatively coupled to the information management apparatus, wherein the second data processor is the data processor, wherein the second computer readable medium is the computer readable medium, and wherein executing the first set of test orders for the first plurality of samples includes executing, by the control system, the first set of test orders for the first plurality of samples received from the information management apparatus, so that the first plurality of samples are processed on one or more instruments in communication with the control system. The first computer readable medium may comprise code, executable by the first data processor, to cause the first data processor to perform a method including: receiving the first set of test orders for the plurality of samples; and providing the first set of test orders to the control system. The second computer readable medium comprises code, executable by the second data processor, to cause the second data processor to perform a method including: receiving the first plurality of test results from the one or more instruments corresponding to the first set of test orders; providing the first plurality of test results to the information management apparatus; receiving the input data from the information management apparatus; after generating the one or more processing rules, receiving, by the control system from the information management apparatus, additional test orders for an additional plurality of samples; and after generating the one or more processing rules, executing, by the control system, the additional test orders for the additional plurality of samples, so that the additional plurality of samples are processed on the one or more instruments in communication with the control system according to the one or more generated processing rules.

Another embodiment of the present disclosure is directed to non-transitory computer readable media, the non-transitory computer readable media comprising code, executable by one or more data processors, to implement a method comprising: executing a first set of test orders for a first plurality of samples; processing the first plurality of samples to obtain a first plurality of test results; and generating one or more processing rules based at least on input data and the first plurality of test results.

These and other embodiments of the present disclosure are described in further detail below.

DETAILED DESCRIPTION

Figure 1:
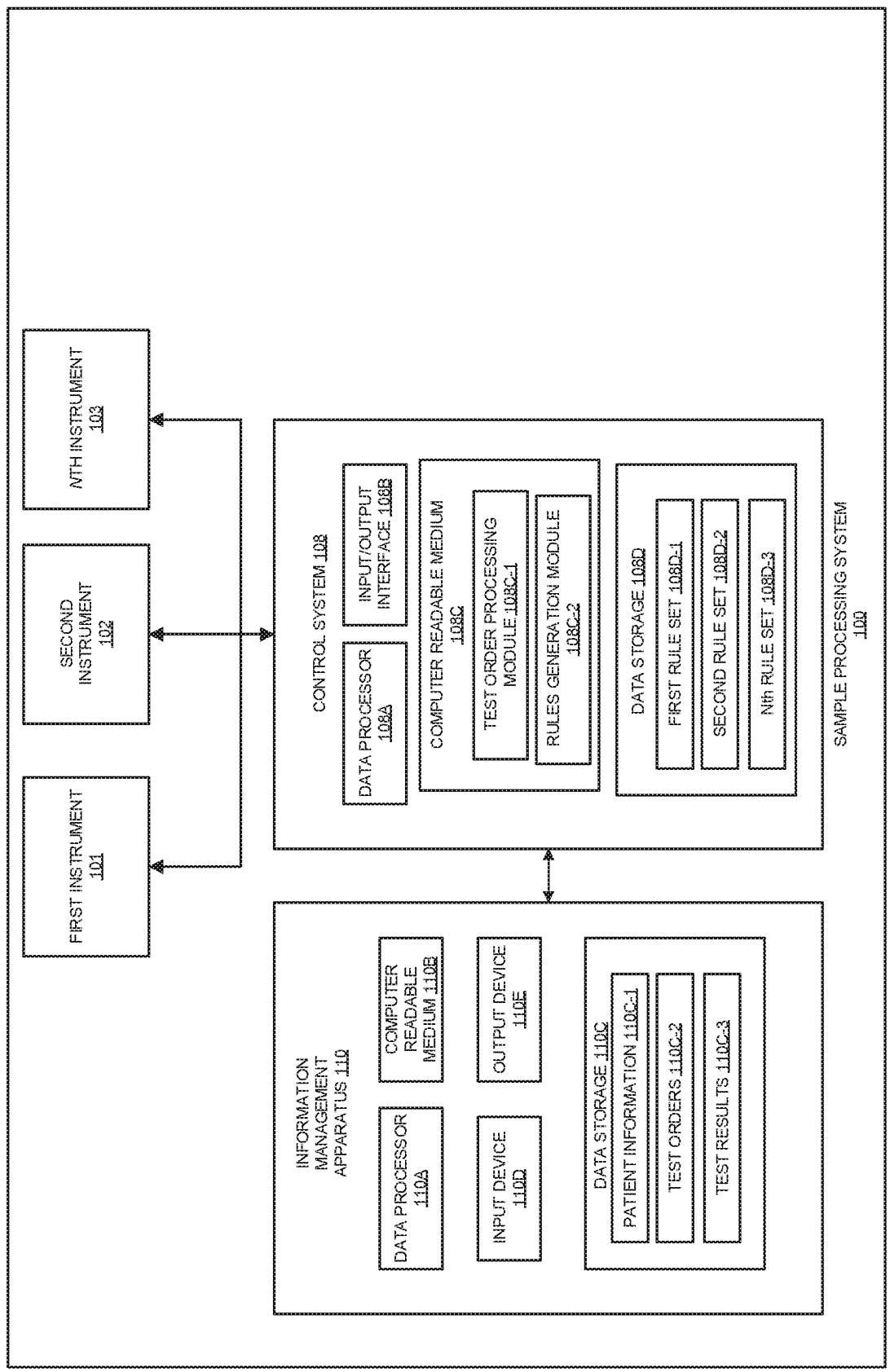
FIG. 1 shows an exemplary block diagram of a sample processing system, in accordance with embodiments of the present disclosure.

The term "instrument" or "analyzer" may include any suitable device that is capable of analyzing or processing a biological sample. Examples of analyzers include PCR machines, flow cytometers, mass spectrometers, immunoanalyzers, hematology analyzers, microbiology analyzers, and/or molecular biology analyzers. In particular, an immunoanalyzer can include an instrument on which immunoassays have been automated. Immunoassays may refer to a laboratory method used to determine the amount or concentration of an analyte in a sample based on the interaction of antibodies with antigens. A mass spectrometer may include instruments which can measure the masses and relative concentrations of atoms and molecules and can be used to elucidate the chemical structures of molecules, such as peptides and other chemical compounds.

The term "sample" can refer to something to be analyzed. A "sample" include biological or chemical samples. A "biological sample" may include organisms or tissue, as well as any solids, liquids, or gases that are biological in origin, as well any solids, liquids, or gases that contain organisms/tissue/analytes that are biological in origin. For instance, examples of biological samples that may be a biological fluid include, but are not limited to, blood, plasma, serum, or other bodily fluids or excretions, such as but not limited to saliva, urine, cerebrospinal fluid, lacrimal fluid, perspiration, gastrointestinal fluid, amniotic fluid, mucosal fluid, pleural fluid, sebaceous oil, exhaled breath, and the like. Another example of a biological sample that may be considered a biological fluid is a solution containing nucleic acids (e.g., DNA/RNA) associated with an individual.

The term "analyte" may include a substance whose presence, absence, or concentration is to be determined according to embodiments of the present disclosure. Typical analytes may include, but are not limited to organic molecules, hormones (such as thyroid hormones, estradiol, testosterone, progesterone, estrogen), metabolites (such as glucose or ethanol), proteins, cholesterols, lipids, carbohydrates and sugars, steroids (such as Vitamin D), peptides (such as procalcitonin), nucleic acid segments, biomarkers (pharmaceuticals such as antibiotics, benzodiazepine), drugs (such as immunosuppressant drugs, narcotics, opioids, etc.), molecules with a regulatory effect in enzymatic processes such as promoters, activators, inhibitors, or cofactors, microorganisms (such as viruses (including EBV, HPV, HIV, HCV, HBV, Influenza, Norovirus, Rotavirus, Adenovirus etc.), bacteria (H. pylori, Streptococcus, MRSA, C. diff., Ligionella, etc.), fungus, parasites (plasmodium, etc.), cells, cell components (such as cell membranes), spores, nucleic acids (such as DNA and RNA), etc. Embodiments of the present disclosure can also allow for the simultaneous analysis of multiple analytes in the same class or different classes (e.g. simultaneous analysis of metabolites and proteins). In embodiments of the present disclosure, the analysis of a particular analyte such as a biomarker may indicate that a particular condition (e.g., disease) is associated with a sample that contains the analyte.

The term "test result" may include measurement values or specific values that are obtained in relation to an analysis or processing of a biological sample. The test result may be determined by one or more instruments, or by an information management apparatus that obtains data from the instruments. For example, a test result associated with a biological sample being analyzed may be an amount or concentration of cholesterol. Test results may be in the form of raw data from an instruments, or may be in form of data that is derived from raw data. In some cases, derived data can be more readily interpreted by system users than raw data.

A "characteristic" of a biological sample may include a property of the biological sample. The property of the sample may relate to the presence, absence, or quantity of components (e.g., organisms, proteins, etc.) in the sample. Characteristics of biological samples may also relate to disease conditions that might or might not be associated with the biological samples. For example, characteristics of biological samples may include whether or not those biological samples are associated with diseases such as Alzheimers, cardiac disease, breast cancer, colorectal cancer, prostate cancer, ovarian cancer, lung cancer, pancreatic cancer, bladder cancer, and heptatocellular cancer. A characteristic of the biological sample may also pertain to a physical property of the biological sample, such as the color or appearance of the biological sample.

The term "ruleset" may include one or more processing rules for automated decision making associated with the testing and handling specific types of biological samples. In some cases, there may be multiple rulesets and each ruleset may correspond to a particular entity (e.g., a laboratory) performing testing on biological samples. The processing rules may include rules and thresholds for validating samples or flagging samples for additional testing/review.

The processing rules may also include rules for handling samples, detection ranges needed to meet orders, etc.

The term "patient information" can include any suitable data related to a patient. Patient information may include, but is not limited to, at least the following types of information: demographic information (name, address, phone), biometric information, patient ID information (unique identifier used to tag samples), imaging information (x-ray, CT, MRI, US), surgical information, pharmaceutical information (e.g., specific drugs a patient is taking or should take and in what dose), billing information, EMR information, physician generated information (e.g., vital signs, observations, medical changes), and historical patient information (e.g., drug levels being monitored, chronic disease information, information about adverse drug reactions, etc.).

The term "test order" may include any suitable type of instruction for analyzing or processing a biological sample (e.g., via an instrument). Exemplary test orders may include patient information associated with biological samples, the patient or health care providers requesting the testing of the biological samples, tests to be performed on the biological samples (e.g., the detection of the presence or absence of specific analyte(s)), and the expected processing times associated with the biological samples. Test orders may also specify specific types of instruments to use to analyze the biological sample.

The term "instrument" may include any suitable device that can act on a sample. An instrument may typically produce one or more measurement values after processing a sample. Examples of instruments may include immunoanalyzers, mass spectrometers, biochemical analyzers, chemical analyzers, flow cytometers, etc. Other examples of instruments may include aliquotters, sample storage units, sample preparation units, etc.

Laboratory testing of biological samples can be performed by a sample processing system, which can include a control system (sometimes referred to as "middleware") usable for automating various aspects of the testing workflows. In particular, the control system may be responsible for receiving orders/instructions to carry out testing, determining the appropriate testing workflow and instruments to use based on the instructions, controlling the operation of the instruments, and analyzing and processing the test results.

This automation can be governed by a set of configurable processing rules defined in a ruleset, which provides each laboratory the ability to configure the control system to perform certain actions when certain conditions are met. A single laboratory may employ hundreds or thousands of such rules in order to automate or streamline the testing of biological samples. As just one example, some processing rules may set forth a set of conditions or criteria under which the test results for a biological sample are automatically validated. Validation is typically something that must be performed before test results associated with a biological sample are returned to a requesting party (e.g., a referring physician or medical practitioner). Thus, autovalidation rules can be configured for automatically distinguishing between certain test results or biological samples that need additional review or testing (and flagging those samples) and test results or samples that do not need additional review or testing and can be returned to the requesting party immediately.

If provided enough data, the control system may be able to derive patterns from historical test results and the historical testing (and other actions) performed on the biological samples. The control system may use these patterns to automatically generate processing rules that can be implemented to automate decisions in the future testing of samples. In some cases, the generated processing rules may include autovalidation rules that can be used to reduce the amount of human oversight and review needed by increasing the percentage of test results that are automatically validated and returned to the requesting party.

The use of automatically generated processing rules in testing biological samples may provide numerous benefits. For instance, laboratory personnel would spend a lot less time manually configuring rules and a lot fewer laboratory personnel would be needed to oversee the testing of a large number of samples. Furthermore, manually defining processing rules may mean the effectiveness of the processing rules are dependent on the skill level of the person writing the rule, and the large difference between skill levels may mean that there is huge variation in the effectiveness of manually defined processing rules as compared to automatically generated processing rules. Additionally, automatically generating processing rules serves as a better mechanism for keeping rulesets up to date (e.g., if the testing practice or policies change at a particular laboratory).

FIG. 1 shows a high level block diagram of sample processing system 100 according to an embodiment of the present disclosure. In some embodiments, sample processing system 100 comprises a plurality of instruments. The plurality of instruments may include first instrument 101, second instrument 102, and so forth, all the way up to Nth instrument 103. Although three instruments are illustrated in FIG. 1, it is understood that there may be fewer than three instruments or greater than three instruments in other embodiments of sample processing system 100.

In some embodiments, sample processing system 100 may include control system 108 that may be communicatively and operatively coupled to instruments 101, 102, 103. Sample processing system 100 may also include information management apparatus 110. There may be input/output interfaces present in each of these components that allow for data transmission between the illustrated devices and components. Although a separate control system 108 and a separate information management apparatus 110 are illustrated in FIG. 1, it is understood that they can be incorporated into a single computer system in other embodiments of the present disclosure. Further, the software running information management apparatus 110 and control system 108 may be local or may run one or more remote server computers (e.g., in the cloud).

In some embodiments, control system 108 can control and/or transmit and messages or instructions to and from instruments 101, 102, and 103, and/or information management apparatus 110. Control system 108 may comprise data processor 108A, input/output interface 108B, non-transitory computer readable medium 108C, and data storage component 108D, coupled to data processor 108A. Non-transitory computer readable medium 108C may comprise code, executable by data processor 108A to perform the functions described herein. Although control system 108 is depicted as a single entity in FIG. 1, it is understood that the control system may be present in a distributed system or in a cloud-based environment. Non-transitory computer readable medium 108C may be a second computer readable medium. The second computer readable medium may comprise code, executable by data processor 108A to perform a method including a) executing a first set of test orders for a first plurality of samples from the information management apparatus, so that the first plurality of samples are processed on one or more instruments in communication with the control system; b) receiving a first plurality of test results from the one or more instruments corresponding to the plurality of test orders; c) providing the first plurality of test results to the information management apparatus; d) receiving, by the control system, input data from the information management apparatus; e) generating one or more processing rules based at least on the input data and the first plurality of test results; f) receiving additional test orders for an additional plurality of samples from the information management system; and h) executing the additional test orders for the additional plurality of samples, so that the additional plurality of samples are processed on the one or more instruments in communication with the control system according to the one or more generated processing rules.

Data processor 108A may be a second data processor and may include any suitable data computation device or combination of such devices. An exemplary data processor may comprise one or more microprocessors working together to accomplish a desired function. Data processor 108A may include a CPU that comprises at least one high-speed data processor adequate to execute program components for executing user and/or system-generated requests. The CPU may be a microprocessor such as AMD's Athlon, Duron and/or Opteron; IBM and/or Motorola's PowerPC; IBM's and Sony's Cell processor; Intel's Celeron, Itanium, Pentium, Xeon, and/or XScale; and/or the like processor(s).

Computer readable medium 108C and data storage 108D may be any suitable device or devices that can store electronic data, such as one or more memory chips, disk drives, and so forth, which typically operate using any suitable electrical, optical, and/or magnetic mode of operation.

Computer readable medium 108C may comprise code, executable by data processor 108A to perform any suitable method. In some embodiments, computer readable medium 108C may include code for test order processing module 108C-1 and rules generation module 108C-2. In some embodiments, test order process module 108C-1 may be configured to take test orders received by control system 108 (e.g., from information management apparatus 110) and process those test orders to send to the instruments in order to carry out the instructions specified in those test orders. In some embodiments, rules generation module 108C-2 may be configured to determine patterns from historical test results and automatically generate processing rules based off those patterns. In the figure, the historical test results may be shown as test results 110C-3 stored with information management apparatus 110, although in some embodiments, historical test results may be stored with control system 108 without containing any personally identifiable information.

Data storage component 108D may be internal (as shown) or external to control system 108. Data storage component 108D may include one or more memories including one or more memory chips, disk drives, etc. Data storage component 108D may include various rule sets, such as first rule set 108D-1, second rule set 108-D2, and so forth, all the way up to Nth rule set 108-D3. These rule sets may contain processing rules and parameters that relate to the operation of an instrument, such as rules associated with analyzing and processing biological samples. These rules may include detection ranges for different instruments, processing logic for different instruments, and so forth. The rules may include static rules (e.g., perform 'X' action in 'Y' condition) and/or dynamic rules. As noted above, rule sets may include one or more rules that can be used to determine which instrument or combination of instruments to use to analyze or process a biological sample. The rules may be associated with the biological sample and/or may incorporate data unrelated to the specific biological sample.

In some embodiments, information management apparatus 110 may be coupled to control system 108, and information management apparatus 110 may be configured to (i) store patient information, (ii) receive one or more test orders for the biological sample, and (iii) receive the one or more test results associated with the biological sample from the plurality of instruments 101, 102, 103.

Information management apparatus 110 may comprise data processor 110A (which may be a first data processor) and non-transitory computer readable medium 110B. Computer readable medium 110B may comprise code for causing data processor 110A to receive, from instruments 101, 102, 103, the one or more measurement values for the biological sample. In some embodiments, data processor 110A may also compare the measurement values to patient information 110C-1 stored in a data store in data storage 110C, and provide an output after comparing. Computer readable medium 110B may also comprise, code executable by data processor 110A to perform a method including receiving the test orders for the plurality of samples; and providing the test orders to the control system. Data processor 110A and non-transitory computer readable medium 110B may be of the same or different type than data processor 108A and computer readable medium 108C in control system 108.

In some embodiments, information management apparatus 110 may also comprise data storage 110C, which may store patient information 110C-1, test orders 110C-2, and test results 110C-3. Information managment apparatus 110 may also include one or more input devices 110D and output devices 110E. Input devices may include touchscreens, keyboards, pointers, microphones, etc. Output devices 110E may include speakers, displays, and tactile devices.

In some embodiments, information management apparatus 110 may be configured to compare the presence or absence of a drug or metabolite in a biological sample, as determined by instruments 101, 102, 103 to patient information 110C-1 in data storage 110C. As a result of this comparison, an output may be provided by information management apparatus 110 (e.g., to a user, such as a medical practitioner) via an output device such as a display coupled to data processor 110A.

The output may be of any suitable type. For example, the output may relate to a report that combines the measurement values from instruments 101, 102, 103, with patient information 110C-1 such as the name of the patient or medical record number of the patient. In other embodiments, the output may include the result of a comparison of any or proposed medications of the patent to any measurement values or it may include a diagnosis or recommendation based upon the measurement values obtained from the instruments and patient information 110C-1.

In some embodiments, information management apparatus 110 may include a laboratory information system (LIS) or a hospital information system (HIS). In some embodiments, those terms may be used interchangeably with information management apparatus 110. In some embodiments, control system 108 may include middleware for controlling and automating the operation of the instruments.

Instruments 101, 102, 103, may be connected directly to the LIS over a network. Data (e.g., measurement values) generated by the instruments can be transmitted to the LIS or HIS. The LIS, with an information system interface, may allow for communications between the LIS and the middleware hub. In some implementations, the middleware hub may provide additional instructions to instruments 101, 102, 103 in order to create, cancel, or modify test orders for the instruments to execute. In some embodiments, the middleware hub may include control system 108 or may include software running on control system 108, such that control system 108 has the role of controlling and automating the operation of instruments 101, 102, 103.

In some embodiments, the rule sets (e.g., rule sets 108D-1, 108D-2, 108D-3) may each correspond to a particular entity (e.g., a laboratory). Thus, the control system 108 with its multiple rule sets may be configured to handle testing of biological samples for numerous laboratories. In other embodiments, control system 108 may be implemented with only a single laboratory, and thus there may only be one rule set available in data storage 108D. In some embodiments, the different rule sets can be created for different sample types, different types of patients, etc.

In some embodiments, a rule set (e.g., rule sets 108D-1, 108D-2, 108D-3) may contain a set of processing rules. Examples of processing rules may include conditional rules, which specify for an action to be performed upon some pre-specified condition being met. For example, conditional rules may specify that if an instrument performs a test and the resulting value is less than, equal to, or greater than a threshold value, then perform a certain action. An example of an action could be to flag the test result and not send the result to the LIS (e.g., the information management apparatus). Thus, an example of a specific conditional rule may be that "if the result value of test T is greater than threshold X, flag the result and do not send it on to the LIS".

A rule set may have any number of rules associated with it. In some embodiments, a rule set may have hundreds or even thousands of rules defined. These processing rules may enable portions of the workflow performed by the components of sample processing system 100. These rules allow the entities (e.g., laboratories) employing the sample processing system 100 to automate their workflows, reduce their staff, and improve the turnaround time needed to analyze and process biological samples. Each laboratory may have their own rule set with rules that are very specific to that laboratory. Those rules may define thresholds, test menus, exception workflows, and so forth, associated with biological sample testing performed at that laboratory.

An example rule set employed by a laboratory may also specify autoverification conditions for permitting test results to progress to the next stages of the workflow if certain conditions (e.g., such as thresholds) are met. The combined 'effect' of various autoverification conditions specified in the rule set may vary depending on how many autoverification rules there are (e.g., how many different autoverification rules have been automatically generated) and how strict the autoverification conditions are for those rules. For instance, in some embodiments, the rule set employed by a laboratory may result in the laboratory automatically sending about 80% of test results to the information management apparatus (e.g., information management apparatus 110 shown in FIG. 1), with the remaining 20% of results being flagged for further examination by laboratory staff. In some embodiments, a rule set employed by a laboratory may have an autoverification rate of 95% or greater, which means that the laboratory is automatically sending about 95% or more of test results to the information management apparatus.

Thus, in various embodiments, the autoverification rate may vary from 5% to 98% depending on the rules, which can be automatically generated via the methods described herein and/or specified by users (e.g., laboratory staff). However, the more reliant the overall ruleset is on rules specified by users, the more dependent the autoverification rate will be on the rule-writing skill level of the user and how strict the autoverification conditions are. In some embodiments, users may be able to write rules to be added to the rule set using SQL or various software tools that provide a graphical user interface and/or a rule library (with pre-built rules) for easily building, changing, and customizing rules. However, there may be a tremendous time and knowledge burden involved in having users generate all the rules that go into a rule set; it can take many weeks and many hours of meetings and workshops to define and implement rules within the rule set. Having AI or an automated algorithm generate rules automatically based on past test results and actions would relieve that burden and make it easier to increase the autoverification rate.

Figure 2:
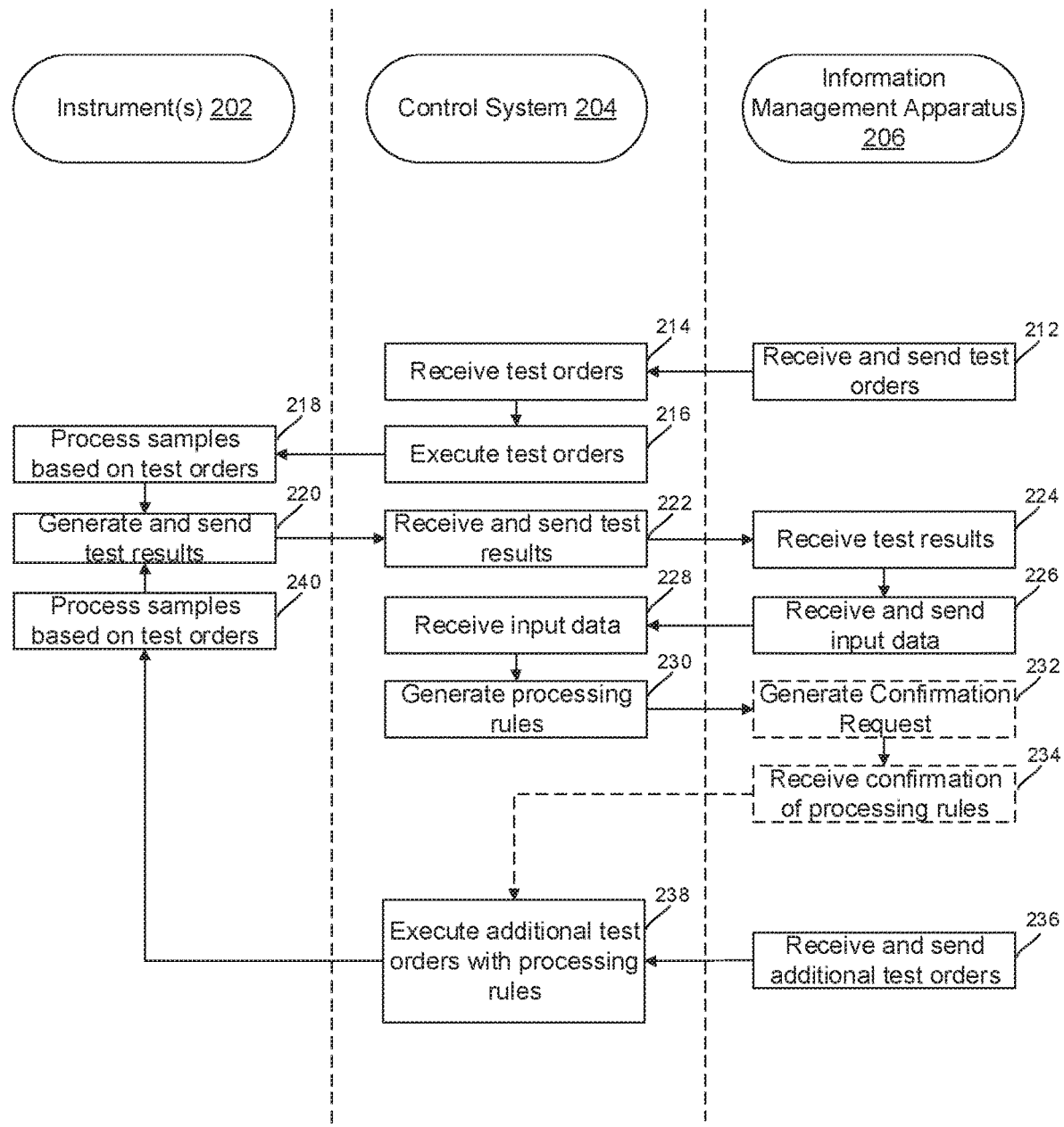
FIG. 2 shows an exemplary flowchart illustrating a sample processing system performing testing with automatically generated processing rules, in accordance with embodiments of the present disclosure.

FIG. 2 illustrates a system flowchart for how processing rules are automatically generated and incorporated into a rule set.

At block 212, information management apparatus 206 (e.g., information management apparatus 110 shown in FIG. 1) may receive and send a test order to control system 204, which will receive the test order at block 214. This order may originate from a user, who will often be a medical professional (e.g., a physician or nurse), laboratory staff, or a patient (e.g., in the case where the patient is ordering testing to be done on their own behalf, such as via an online platform). In some embodiments, the test order may be generated at information management apparatus 206. For example, a user may supply the test order to information management apparatus 206 by entering the test order via an interface of information management apparatus 206. In some embodiments, the user may enter the test order using input device 110D shown in FIG. 1. In some embodiments, the test order may be generated apart from information management apparatus 206 and sent to information management apparatus 206. For instance, the test order may be generated in electronic medical record (EMR) software or systems and sent to information management apparatus 206. The test order may be sent to control system 204 in a variety of ways. For instance, information management apparatus 206 may be communicatively coupled to control system 204 via local area network (LAN) or wide area network (WAN). Alternatively, information management apparatus 206 may be communicatively coupled to control system 204 via the Internet, which may be especially helpful if control system 204 is implemented using distributed computing or a cloud cluster. It should be noted that, in some embodiments, the test order may be generated at control system 204, and thus the workflow could be performed without block 212 shown in FIG. 2.

At block 214, control system 204 may receive the test orders. At block 216, control system 204 may execute the test orders by sending the test orders to one or more instruments 202. The test orders may instruct one or more instruments 202 to analyze and process biological samples.

At block 218, instruments 202 may process the biological samples based on the received test orders. In some embodiments, instruments 202 may have to be supplied with biological samples beforehand. For instance, a user may have to manually feed a biological sample into the instrument.

At block 220, instruments 202 may generate test results from processing the biological samples and then send those test results to control system 204.

At block 222, control system 204 may receive the test results. Control system 204 may then provide the test results to information management apparatus 206.

At block 224, information management apparatus 206 may receive the test results. The test results may be provided to the user (e.g., a physician or patient) for review.

At block 226, information management apparatus 206 may receive input data from the user. Information management apparatus 206 may send that input data to control system 204. The input data may be any suitable data that may be responsive to the test results for a sample. For example, in some embodiments, input data may be in the form of new test order for a same sample that was tested and for which a test result was received. In other embodiments, the input data may be in the form of data that is derived from many test orders. For example, the data from many test orders for samples that have already received test orders can be used as input data.

At block 228, control system 204 may receive the input data sent from information management apparatus 206. In some embodiments, the user may provide input data directly to control system 204 rather than through information management apparatus 206. Thus, the workflow could be performed without block 226 shown in FIG. 2.

At block 230, control system 204 may automatically generate processing rules for addition to the rule set. The automatic generation of processing rules is described in additional detail with regards to FIG. 4. In some embodiments, following the generation of the processing rules, control system 204 may send the generated processing rules to information management apparatus 206. At block 232, information management apparatus 206 may optionally generate a confirmation request and display it to the user. The confirmation request may inform the user of the generated processing rule and seek the user's approval to enact the generated processing rule. In some embodiments, the confirmation request may be displayed in the form of a prompt, such as the one shown in FIG. 3.

In some embodiments, at block 234, information management apparatus 206 may receive confirmation of the generated processing rule from the user. Information management apparatus 206 may notify control system 204 that the generated processing rule was approved to be added to the ruleset.

At block 236, information management apparatus 206 may receive an additional test order and send it to control system 204, which will receive the additional test order at block 238.

At block 238, control system 204 may execute the additional test orders with the generated processing rule that has been added to the rule set (if the rule is relevant to the additional test order).

At block 240, instruments 202 may receive the additional test orders and process the biological sample according to the additional test orders. The results can be sent to control system 204, to serve as additional data points for the generation of processing rules. Thus, the workflow depicted in FIG. 2 may serve as an iterative cycle, in which control system 204 is continually generating processing rules to add to the rule set and updating existing processing rules as it receives more and more test results that serve as input data points used in generating processing rules.

Figure 3:
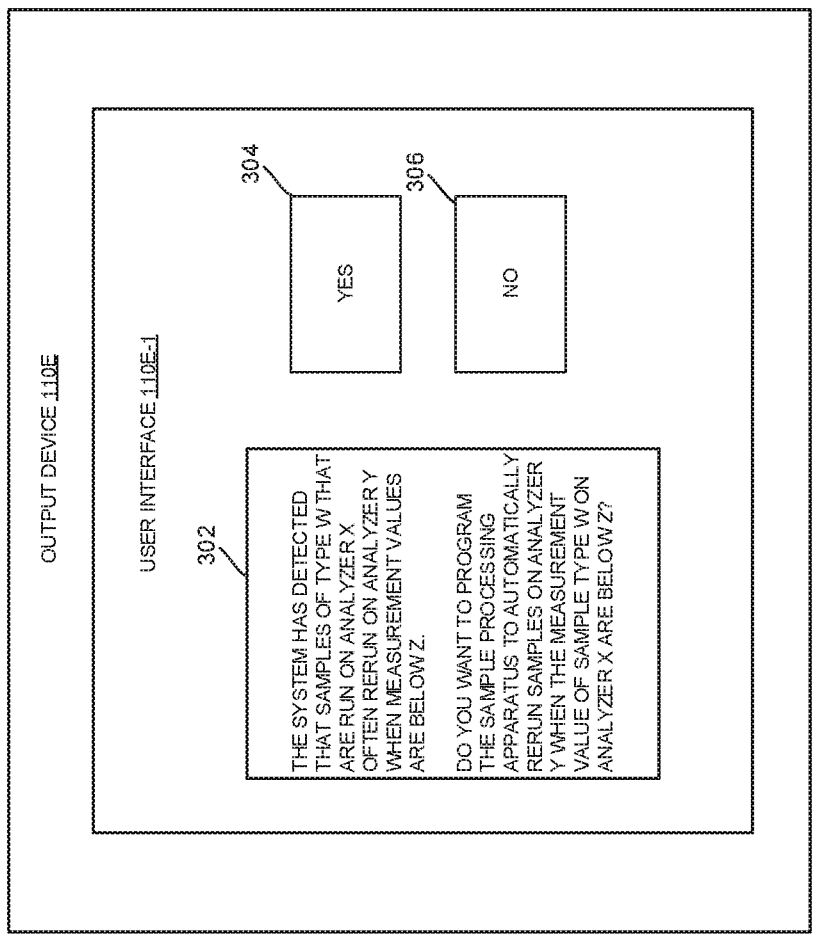
FIG. 3 shows an example user interface of a prompt displaying a confirmation request associated with generated processing rule, in accordance with embodiments of the present disclosure.

FIG. 3 illustrates an example user interface of prompt displaying a confirmation request for a generated processing rule.

As shown in the figure, there may be output device 110E (e.g., as part of information management apparatus 110) that provides a display viewable by a user, such as a medical practitioner or laboratory staff, interacting with information management apparatus 110. In some embodiments, output device 110E can be a monitor or screen that can display a user interface, such as user interface 110E-1.

User interface 110E-1 may be used to display prompt 302 to the user associated with a confirmation request, such as the confirmation request generated at block 232 in FIG. 2. In other words, prompt 302 may be used to notify the user of a generated processing rule and seek confirmation from the user to implement that rule into the ruleset for use in automating decisions made in future testing.

For instance, in the figure shown, prompt 302 notifies the user that the control system of the sample processing system has detected that samples of type 'W' tested by analyzer 'X' are often rerun on analyzer 'Y' when the test result or measurement values obtained from analyzer 'X' are below a threshold 'Z'. The control system may determine this based on historical data associated with numerous past tests conducted on samples of type 'W'. Accordingly, the control system may generate a processing rule to automatically rerun samples of type 'W' on analyzer 'Y'

If the user selects yes button 304, then the control system may save that generated processing rule into the ruleset, where it will take effect for future testing. For instance, after the user selects yes button 304 for the prompt in the previous example, then for the next sample of type 'W' tested by analyzer 'X' that has a measurement value below threshold 'Z', the control system will automatically order analyzer 'Y' to perform testing on that sample without needing any additional manual input from the user.

If the user selects no button 306, then the control system will not save that generated processing rule into the ruleset. In some embodiments, once the user selects no button 306, that specific generated processing rule will not be presented to the user again unless the user accesses settings via the user interface, which will provide a list of rejected processing rules that were not implemented. In some embodiments, even if the user rejects the generated processing rule, the control system may continue to prompt the user with that specific processing rule at specific time intervals (e.g., X days later, then Y days later if canceled again, then Z days later if canceled yet again).

Figure 4:
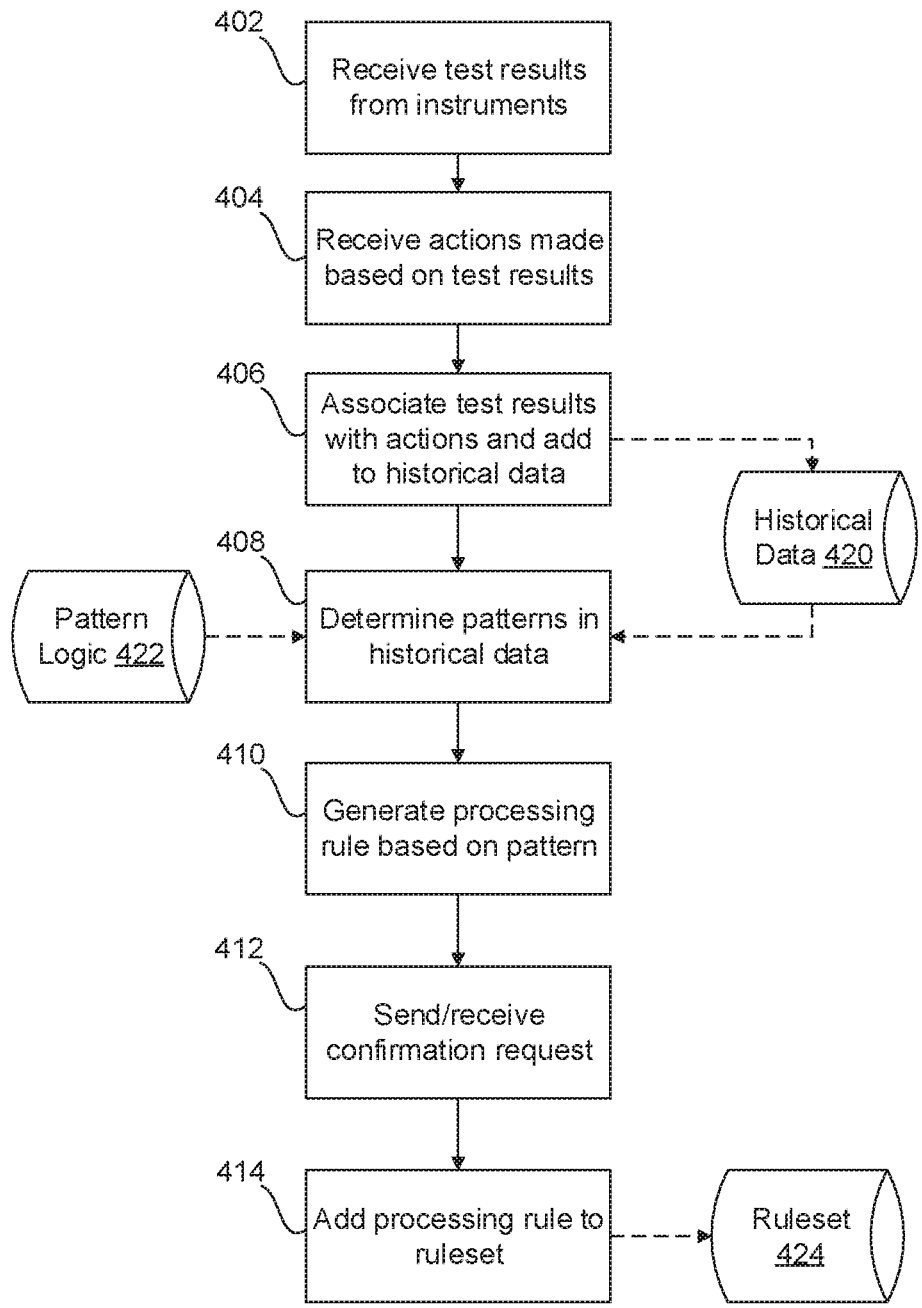
FIG. 4 shows an exemplary flowchart illustrating the automatic generation of processing rules, in accordance with embodiments of the present disclosure.

FIG. 4 shows a flowchart illustrating the automatic generation of processing rules, in accordance with embodiments of the present disclosure. In particular, FIG. 4 illustrates processing rule generation from the perspective of the control system. The blocks of the flowchart depicted in FIG. 4 may be similar in nature to blocks 222, 228, 230, and 238 shown in FIG. 2.

At block 402, for each biological sample being tested, the control system may receive test results from one or more instruments testing that biological sample. Generally, the test results will be obtained from executing the received test order associated with that biological sample. The control system may receive these test results directly from the instruments.

At block 404, for each biological sample that has been tested, the control system may receive input data (e.g., entered by a user, such as a medical practitioner, with an information management apparatus) describing actions or decisions made based on the characteristics of the sample, the testing parameters, and the test results associated with the sample. For example, test results for a sample may include a value that is determined to be less than a threshold value. As a result of that value being less than the threshold value, the test result may be flagged for further review. Information regarding the flag for further review may be considered an example of input data. Alternatively, the test result may be flagged for additional testing using a different instrument. The input data associated with that sample would indicate that the test result was flagged for review or additional testing specifically because the measured value was determined to be less than a threshold value. In other words, the input data associated with a particular biological sample may inform how test results for the sample were obtained, how the test results were interpreted, and which actions were performed as a result of that test sample. In some cases, input data may be quite extensive (e.g., such as if a sequence of actions, 'X', 'Y', and 'Z' were performed based on the test results and the fulfilment of certain conditions) and may log, in chronological order, the actions performed using the sample and test results. In other embodiments, input data may comprises a second plurality of test orders corresponding to a second plurality of samples of a particular type that have been entered into the information management apparatus. For example, information management apparatus 110 may automatically recognize that the second plurality of samples are samples that were previously run by the system, but are being re-run as part of a re-test or reflux testing process (e.g., the samples may be tied to the same patients). The sample processing system may automatically infer from this data that the entity operating the sample processing system a re-test or reflex test may be appropriate when testing samples of that particular type.

At block 406, for each biological sample that has been tested, the control system may combine or associate the test results for the sample with the input data (e.g., log of actions) associated with that sample. The combined data can be added to historical data 420, which serves as a database for past biological samples, their historical test results, and any actions taken in connection with those historical test results. In some cases, the input data for a sample may already include the test results associated with that sample, which means the control system can just save the input data. As a more concrete example, consider the scenario that patients may frequently have their blood (e.g., a biological sample) tested for cholesterol levels. Historical data 420 may include, for each patient that had this testing performed, the cholesterol level of that patient, along with what actions were taken based on the measured cholesterol level. For example, historical data 420 may describe patient 'X' as having an abnormally high cholesterol level of 'Y', which resulted in another test being performed with instrument 'Z' to confirm the cholesterol measurement. By constantly adding new test results to the historical data, patterns can be either be defined based on data taken from historical timespans or by dynamically factoring in new test results.

At block 408, the control system may look at historical data 420 in order to determine patterns observed with the actions taken for biological samples or test results with similar characteristics. In other words, the control system takes a retrospective review of actions taken upon past results in order to derive processing rules. For instance, the control system may look at all the data associated with instances of testing blood for cholesterol levels as a group in order to identify patterns associated with actions taken based on cholesterol levels. In some embodiments, the control system may look at the entire timespan of available data. In some embodiments, the control system may look at the last month or two of data in order to identify patterns, since laboratory policies and practices may change over time. In some embodiments, the timespan used may depend on the instrument or test being used with the samples. For instance, a laboratory may perform hundreds of measurements of cholesterol levels in a day, which means that data gathered from the last month is likely to be sufficient to discern any significant patterns. However, for more esoteric or uncommon tests, a longer timespan will be required in order to collect more data points for extracting meaningful patterns. The patterns may be identified based on pattern logic 422, which may be configured to identify patterns in various types of scenarios, some of which are explained below.

The identification of patterns can use any suitable machine learning algorithm. Such machine learning algorithms may include unsupervised learning processes including but not limited to k-means, hierarchical clustering, neural networks, etc.

In one scenario, a pattern may be determined if certain actions are routinely taken when a test result or measured value is above or below a given threshold. For example, it may be a common occurrence that a measured value of cholesterol greater than 100 is flagged for additional review, while amounts of cholesterol lower than that 100 threshold are typically validated. This threshold can be determined from seeing the actions taken with the test results of different patients (e.g., patients with cholesterol of 110 or 120 are flagged for additional review, while patients with cholesterol of 85 or 95 are validated). This pattern can be used to support the generation of an autovalidation processing rule at block 410, with any cholesterol test values under 100 being automatically validated. Validation is only one example of an action that could be taken. Any other action typically performed in the testing workflow can be carried out when conditions are met, such as using other instruments to conduct additional tests on a sample based on test results. In addition to a constant value for the threshold, bands of values may be used instead. For instance, if the measured value is within a first band of values (e.g., between 80 to 100) it may be considered acceptable. However, if the value is outside the band it may be considered not acceptable, in which case the generated processing rule at block 410 may have the sample retested or flag the results to be reviewed by a medical practitioner. At the same time, there could be additional bands, such as a second band of values (e.g., between 40 and 140) where a measured value outside the second band of values is so far beyond what is acceptable that it can be attributed to instrumentation error. In the case that the value is outside this second band, the generated processing rule may specify that personnel is notified that the instrument requires calibration or that an alternative test be conducted on the sample using a different instrument. In some embodiments, the patterns and the generated processing rules may be more complicated. For instance, the processing rule may be based on combining the test results for multiple different analytes, which can be obtained using multiple different instruments.

In another scenario, a pattern may be determined if certain actions are routinely taken together or certain conditions are met. For example, it may be the case that if a particular set of three actions are taken, then a fourth action will typically be performed (e.g., of the users who order 'X', 'Y', and 'Z' tests for this type of sample, they also always order test 'A'). With enough data, this kind of relationship can be determined and automatically implemented into a processing rule.

Once the processing rule is generated based off a pattern, at block 412, the control system may send a confirmation request associated with the generated processing rule. For instance, this confirmation request could go to the information management apparatus, which will display to the user (e.g., laboratory personnel or an administrator tasked with selecting processing rules for the ruleset). If the user accepts the proposed processing rule, the confirmation approval will be sent back to the control system, and at block 414 the control system will add the accepted processing rule to ruleset 424, where it can be retrieved and implemented in future testing of samples.

In summary, the process shown in FIG. 4 may have numerous features that improve the quality of the rule set used to make automated decisions in a testing workflow. For instance, historical data from past testing of samples can be saved and used to create an initial rule set, which can be created automatically or may involve user input such that the user can accept or reject proposed rules. In some cases, rules can be "fuzzy" and threshold values do not have to be hard cutoffs. For instance, even if the control system determines that certain actions are being taken in 98% (and not 100%) of the cases in which a sample meets a specific criteria, that relationship may still be detected. Furthermore, the control system may constantly be adding current data (e.g., for new test results being performed on samples) to existing historical data, and the use of current data may improve the complexity of the generated rules that are added to the rule set.

Figure 5:
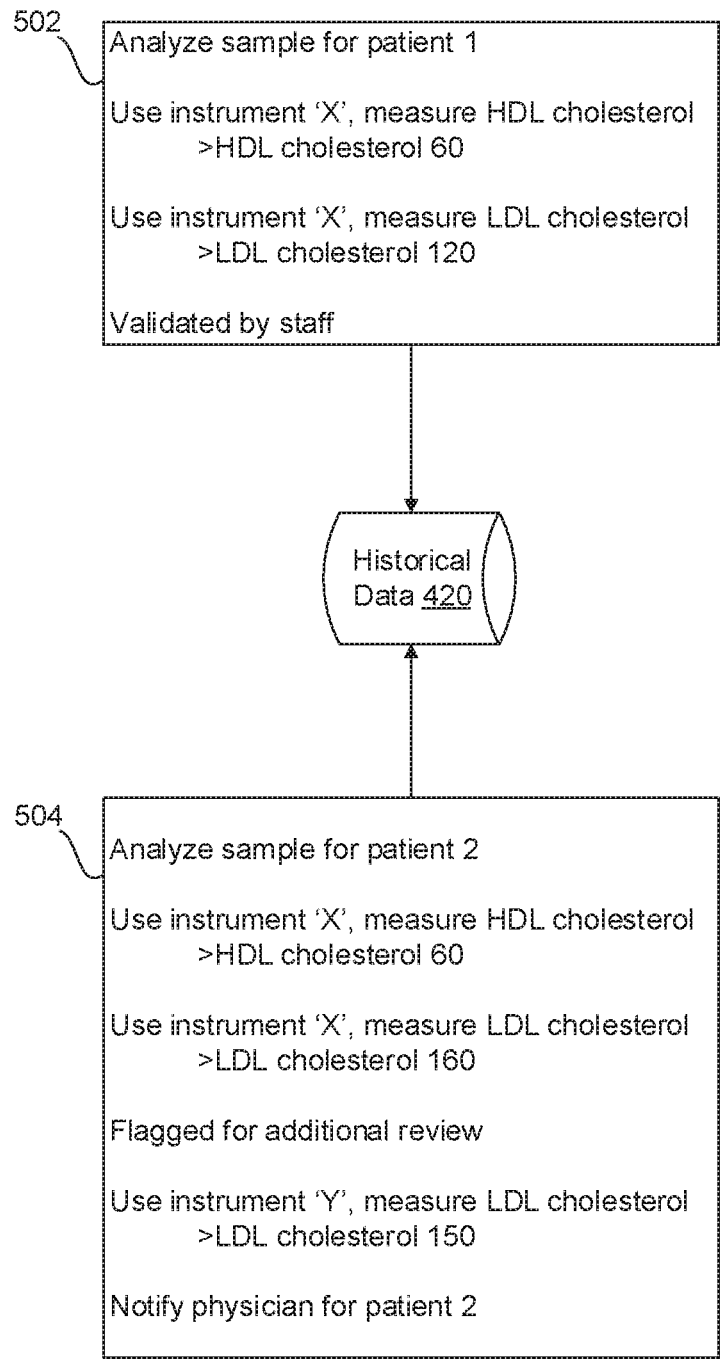
FIG. 5 shows an example data structure for historical data that can be used to identify patterns to generate processing rules, in accordance with embodiments of the present disclosure.

FIG. 5 illustrates an example data structure for historical data that can be used to identify patterns to generate processing rules, in accordance with embodiments of the present disclosure.

As previously mentioned, historical data 420 may include, for the testing of a sample associated with a patient, the test results from any testing along with the actions performed in relation to the testing. FIG. 5 shows records associated with two samples that illustrates an example embodiment of the data structure for how historical data 420 may be stored, in order to allow the test results and any actions performed to be singularly combined into a format that makes it easier to recognize patterns for the automatic generation of processing rules. This is only a single, exemplary embodiment of how historical data 420 may be stored; other ways of storing historical data 420 exist for the purposes of facilitating ease in the generating of processing rules.

In the figure shown, record 502 in historical data 420 corresponds to a sample (e.g., blood) that was tested for patient 1. In practice, the records in historical data 420 may each have their own unique identifiers (e.g., to confirm there are no duplicate records), while all identifying information for the patients may be removed for HIPAA purposes. In some embodiments, record 502 may indicate what kind of sample was analyzed for the patient, such as blood, saliva, and so forth. In some embodiments, record 502 may serve as a chronological record of the actions performed on a sample and the actions listed may have been performed in an order from top to bottom.

For instance, as indicated in record 502, instrument 'X' may have been used to measure HDL cholesterol levels in the blood. That test returned a HDL cholesterol level of 60. Afterwards (or even concurrently), instrument 'X' may also have been used to measure LDL cholesterol in the blood. The test returned a LDL cholesterol level of 120. After attaining those two test results, it can be seen that the sample for patient 1 was eventually validated by laboratory staff.

Record 504 shows a similar array of testing that was performed for a sample (e.g., blood) associated with patient 2. Instrument 'X' was used to measure HDL cholesterol for patient 2, and that test returned a HDL cholesterol level of 60. Afterwards (or even concurrently), instrument 'X' may also have been used to measure LDL cholesterol in the blood, returning a LDL cholesterol level of 160. However, instead of the sample being immediately validated by laboratory staff after those two tests (as was the case in record 502), this sample was flagged for additional review. Instrument 'Y' was then used to measure the LDL cholesterol again, which returned a LDL cholesterol level of 150. After that test, the physician associated with the patient was notified (again, the names of the patient/physician may not be necessary here—only the indication that the physician in this instance was notified).

This data structure for the record may allow patterns to be quickly identified. For example, a search could be performed on all the records in historical data 420 to identify all records that include the three tests "Use instrument 'X', measure HDL cholesterol", "Use instrument 'X', measure LDL cholesterol", and "Use instrument 'Y', measure LDL cholesterol", and record 504 would be part of the results (in this case, even if the search specified that the three tests have to be in that order). Thus, all the records in the search would be instances in which all three of those tests were performed, which may be useful for identifying patterns for processing rule generation (e.g., a fourth test was always performed accompanying those three specific tests). As another example, a search could be performed on all the records in historical data 420 to identify all records that include the test "User instrument 'X', measure LDL cholesterol", and the results of that test and the actions that were performed immediately after that test can be looked at to identify patterns.

From these examples, it can be seen that, in some embodiments, the data structure for the records will contain, in chronological order: (1) the tests performed on the sample and the results from that testing; and (2) the actions performed in-between or following testing. These descriptions can vary in complexity, and may include full-fledged descriptions, pseudo-code, code, and the like. In some embodiments, the records may also contain notes or reasons (e.g., supplied by laboratory staff) that certain actions were performed. For example, record 504 may indicate that the sample was "Flagged for additional review", specifically because the LDL cholesterol was too high or was over a threshold value. This may provide additional information that can be used for identifying patterns to generate processing rules.

Figure 6:
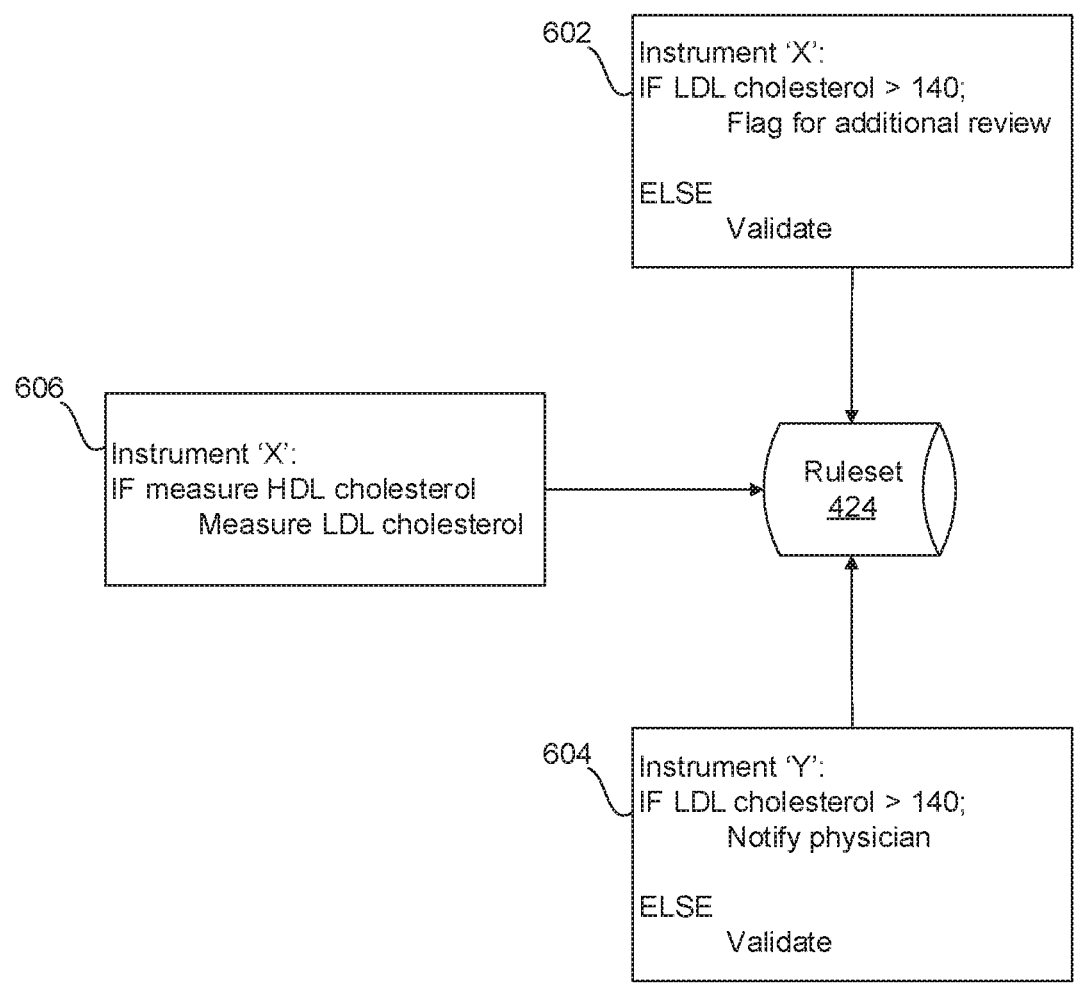
FIG. 6 illustrates an example generated processing rules added to a ruleset, in accordance with embodiments of the present disclosure.

FIG. 6 illustrates example generated processing rules added to a ruleset, in accordance with embodiments of the present disclosure.

In particular, the figure illustrates example processing rules that may have been derived using a set of records that includes records 502 and 504 from FIG. 5. This may be the case if the scenarios indicated in records 502 and 504 in FIG. 5 are representative of frequent occurrences that are encapsulated in numerous records contained in the historical data 420.

For instance, in record 502, the instrument 'X' measures LDL cholesterol at 120, which results in validation by the lab staff. However, in record 504, the instrument 'X' measurement of LDL cholesterol is at 160, which results in the sample being flagged for additional review. If, over many records, samples are flagged for review when the LDL cholesterol measured by instrument 'X' is above 140, while samples are validated when the LDL cholesterol measured by instrument 'X' is below 140, that may result in processing rule 602 being generated. Under processing rule 602, if instrument 'X' measures the LDL cholesterol to be over 140, the sample is flagged for additional review. Otherwise, the sample is validated.

As another example, in record 504, the instrument 'Y' is used to measure LDL cholesterol at 150, which results in the physician being notified. It may be the case that, in many records, the physician is notified if instrument 'Y' is reporting too high of a LDL cholesterol level. For instance, instrument 'Y' might be a very accurate, but expensive, method for measuring LDL cholesterol which makes it well suited for secondary, confirming LDL cholesterol measurements. Thus, in scenarios where the instrument 'Y' reports a high LDL cholesterol level, it is likely that there has already been extensive testing performed and the physician should be notified rather than flagging the sample for additional review or performing more testing. This pattern may result in processing rule 604 being generated. Under processing rule 604, if instrument 'Y' measures a LDL cholesterol level above 140, the physician is notified. Otherwise, the sample is validated.

As yet another example, in both records 502 and 504, instrument 'X' is used to measure both HDL cholesterol and LDL cholesterol. It may be the case that, in many records, instrument 'X' is used to measure both HDL and LDL cholesterol because it is important to interpret both measurements. Thus, instrument 'X' should always be used to measure LDL cholesterol if it is also used to measure HDL cholesterol. This pattern may result in processing rule 606 being generated. Under processing rule 606, if instrument 'X' is used to measure HDL cholesterol, instructions will also be sent for instrument 'X' to measure LDL cholesterol.

Figure 7:
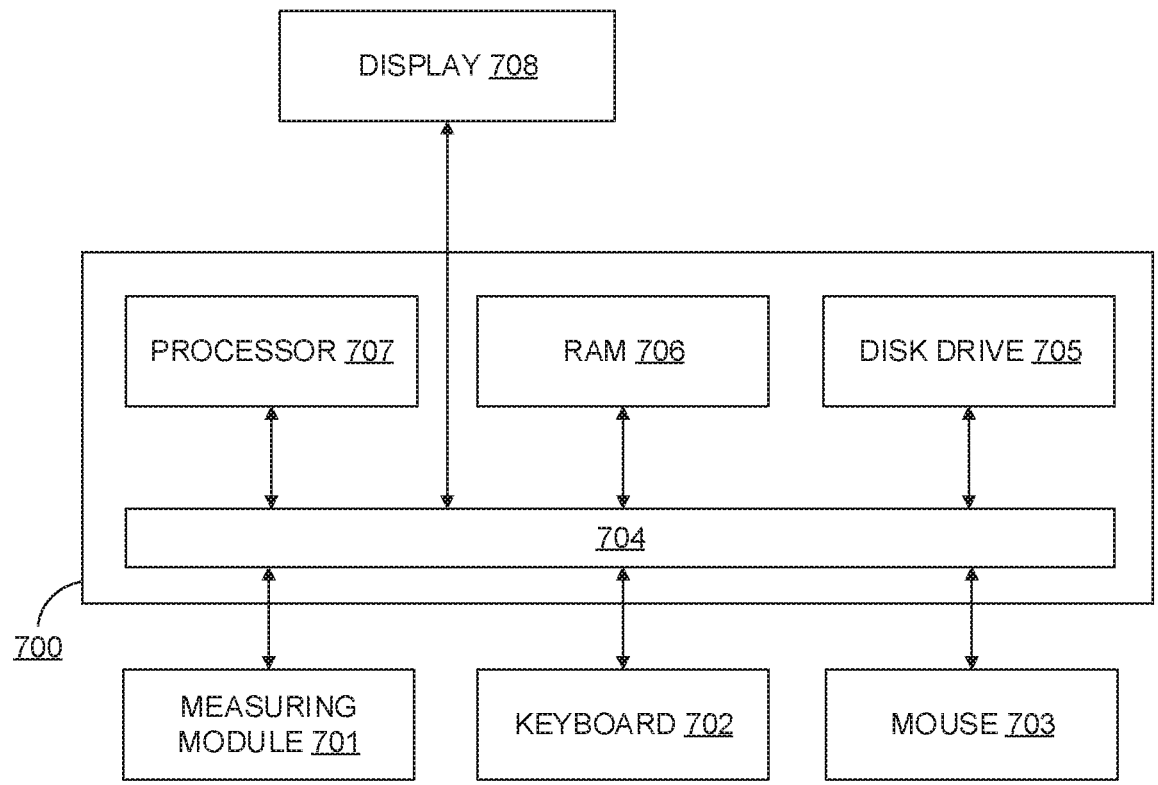
FIG. 7 is a block diagram of a system that can be used to execute various embodiments.

FIG. 7 shows a system including digital computer 700, and a measuring module 701 operatively coupled (which may include electronic coupling) to digital computer 700.

In this example, digital computer 700 may include a variety of typical computer components including system bus 704, one or more disk drives 705, RAM 706, and processor 707, operatively coupled together. Other components can also be present depending on the exact nature of the embodiment. FIG. 7 also shows display 708, keyboard 702, and mouse 703. These components and other components may also be part of the digital computer in some embodiments.

The system can also have measuring module 701 that is used to measure characteristics of selected targets in a sample (e.g., known or unknown). This measuring module may vary between different embodiments of the invention depending on the measurement method selected to measure the target responses. For example, according to one embodiment, the measurement module may conduct a PCR analysis on a sample and may therefore be a real-time PCR apparatus. Real-time PCR apparatuses are commercially available.

In one embodiment of the invention, a sample is placed in measurement module 701 where the sample is processed and characteristics of the selected targets (e.g., the quantities) from the sample are measured. This data (e.g., test results) is then transferred into digital computer 700 along system bus 704, and an appropriate processing rule can be applied to the test results using processor 707. The instructions cause the processor 707 to execute the processing rules (as described above), which may be stored on a computer readable medium such as the RAM 706 or disk drive 705. The output from the test results or the generated processing rules can then be displayed on the display 708 or other output device (e.g., a printer). For example, generated processing rules may be displayed on the display 708 or output in some other manner.

As noted above, in some embodiments, the computer readable media may store or include code which can be executed by the processor to implement a method for analyzing and processing samples in accordance with generated processing rules. In one embodiment, the method may include: executing a first set of test orders for a first plurality of samples, processing the first plurality of samples to obtain a first plurality of test results, and generating one or more processing rules based at least on input data and the first plurality of test results. In some embodiments, this method may be performed by a sample processing system that comprises: an information management apparatus comprising a first data processor and a first computer readable medium; and a control system comprising a second data processor, and a second computer readable medium, the control system communicatively coupled to the information management apparatus. In some embodiments, the code executed by the processor to implement the method may further cause the processor to perform steps for: receiving, by the information management apparatus, the first set of test orders for the first plurality of samples; providing, by the information management apparatus, the first set of test orders to the control system; receiving, by the control system, the first plurality of test results from the one or more instruments corresponding to the first set of test orders; providing, by the control system, the first plurality of test results to the information management apparatus; receiving, by the information management apparatus, the input data from the information management apparatus, receiving, by the control system, the input data from the information management apparatus; after generating the one or more processing rules, receiving, by the control system from the information management apparatus, additional test orders for an additional plurality of samples; and after generating the one or more processing rules, executing, by the control system, the additional test orders for the additional plurality of samples, so that the additional plurality of samples are processed on the one or more instruments in communication with the control system according to the one or more generated processing rules.

Any of the software components or functions described in this application, may be implemented as software code to be executed by a processor using any suitable computer language such as, for example, Java, C++ or Perl using, for example, conventional or object-oriented techniques. The software code may be stored as a series of instructions, or commands on a computer readable medium, such as a random access memory (RAM), a read only memory (ROM), a magnetic medium such as a hard-drive or a floppy disk, or an optical medium such as a CD-ROM. Any such computer readable medium may reside on or within a single computational apparatus, and may be present on or within different computational apparatuses within a system or network.

The above description is illustrative and is not restrictive. Many variations of the present disclosure will become apparent to those skilled in the art upon review of the disclosure. The scope of the present disclosure should, therefore, be determined not with reference to the above description, but instead should be determined with reference to the pending claims along with their full scope or equivalents.

One or more features from any embodiment may be combined with one or more features of any other embodiment without departing from the scope of the present disclosure.

A recitation of "a", "an" or "the" is intended to mean "one or more" unless specifically indicated to the contrary.

All patents, patent applications, publications, and descriptions mentioned above are herein incorporated by reference in their entirety.

What is claimed is:

1. A computer-implemented method for generating one or more processing rules, the method comprising:

executing, by a sample processing system comprising one or more data processors, a first set of test orders for a first plurality of samples;

processing, by the sample processing system, the first plurality of samples using one or more instruments to obtain a first plurality of test results;

receiving, by the sample processing system, the first plurality of test results from the one or more instruments;

receiving, by the sample processing system, and for each sample of the first plurality of samples, input data describing actions or decisions made based on characteristics of the sample;

associating, by the sample processing system, test results of the first plurality of test results for each sample of the first plurality of samples with the input data associated with that sample; and generating, by the sample processing system, one or more processing rules that are used to automate decisions in a testing of samples, based at least on the input data and based at least on the first plurality of test results.

2. The method of claim 1, wherein the sample processing system comprises:

an information management apparatus comprising a first data processor and a first computer readable medium; and a control system comprising a second data processor, and a second computer readable medium, the control system communicatively coupled to the information management apparatus, wherein executing the first set of test orders for the first plurality of samples includes executing, by the control system, the first set of test orders for the first plurality of samples received from the information management apparatus, so that the first plurality of samples are processed on one or more instruments in communication with the control system, wherein the control system performs generating the one or more processing rules, wherein the receiving of input data comprises:

receiving, by the information management apparatus, the input data; and receiving, by the control system, the input data from the information management apparatus, and wherein the method further comprises:

receiving, by the information management apparatus, the first set of test orders for the first plurality of samples;

providing, by the information management apparatus, the first set of test orders to the control system;

receiving, by the control system, the first plurality of test results from the one or more instruments corresponding to the first set of test orders;

providing, by the control system, the first plurality of test results to the information management apparatus;

after generating the one or more processing rules, receiving, by the control system from the information management apparatus, additional test orders for an additional plurality of samples; and after generating the one or more processing rules, executing, by the control system, the additional test orders for the additional plurality of samples, so that the additional plurality of samples are processed on the one or more instruments in communication with the control system according to the one or more generated processing rules.

3. The method of claim 1, wherein generating the one or more processing rules based at least on the input data and the test results, comprises:

grouping a set of test results within the first plurality of test results; and determining at least one threshold based upon the set of test results and the input data, based on seeing the actions taken with the test results of different patients, wherein the actions comprise the test result being either validated or being flagged for review, wherein at least one of the one or more processing rules is an autovalidation processing rule that incorporates the at least one threshold.

4. The method of claim 3, wherein the at least one threshold comprises a lower threshold and a higher threshold.

5. The method of claim 4, wherein the lower threshold and higher threshold are also defined in part by historical sample data in a patient repository.

6. The method of claim 3, wherein the autovalidation processing rule that incorporates the at least one threshold is a rule configured to:

receive a subject test result as input;

determine, based on comparing the subject test results with the threshold, an action selected from a set of actions consisting of:

validating the subject test result and automatically returning the subject test result to a requestor without additional review or testing; and flagging the subject test result for review.

7. The method of claim 1, further comprising, after generating the one or more processing rules:

generating, by the sample processing system, an inquiry requesting a user to confirm use of the one or more generated processing rules for sample processing;

providing, by the sample processing system, the inquiry to the user via an output device in the information management apparatus;

receiving, by the sample processing system, a selection of the one or more generated processing rules; and storing, by the sample processing system, the one or more generated processing rules in a data storage.

8. The method of claim 1, wherein the input data comprises a second plurality of test orders corresponding to a second plurality of samples.

9. The method of claim 1, further comprising:

identifying, by the sample processing system, a set of test results within the first plurality of test results, wherein the test result was measured by a same first instrument;

identifying, by the sample processing system, that the test results of the set of test results have been either validated or flagged for additional review, wherein in the additional review a different, second instrument has been used to perform the measurement; and identifying, by the sample processing system, a threshold value for measurement values for which corresponding test results have been flagged for additional review, wherein at least one of the one or more processing rules is a processing rule that specifies that whenever a test result, measured by the first instrument, is a measurement value above the identified threshold respectively within an identified value range, then the same test is to be repeated by the second instrument.

10. The method of claim 1, wherein generating the one or more processing rules that are used to automate decisions in the testing of samples, based at least on the input data and based at least on the first plurality of test results comprises using an artificial intelligence algorithm to generate the one or more processing rules.

11. The method of claim 1, wherein:
processing the first plurality of samples using one or more instructions to obtain the first plurality of test results comprises, for each sample from the first plurality of samples, performing one or more corresponding tests on that sample; and
the input data used in generating the one or more processing rules comprises, for each sample of the first plurality of samples, input data describing actions or decisions made based on characteristics of that sample determined by performing the one or more corresponding tests on that sample.

12. A sample processing system comprising:
one or more data processors; and
a computer readable medium, the computer readable comprising code executable by the data processor to perform a method including:
  executing, by the one or more data processors, a first set of test orders for a first plurality of samples;
  processing, by the one or more data processors, the first plurality of samples using one or more instruments to obtain a first plurality of test results;
  receiving, by the one or more data processors, the first plurality of test results from the one or more instruments;
  receiving, by the one or more data processors, for each sample of the first plurality of samples, input data describing actions or decisions made based on characteristics of the sample;
  associating, by the one or more data processors, the test results of the first plurality of test results for each sample of the first plurality of samples with the input data associated with that sample; and
  generating, by the one or more data processors, one or more processing rules that are used to automated decisions in a testing of samples, based at least on the input data and based at least on the first plurality of test results.

13. The system of claim 12, wherein the sample processing system further comprises:
an information management apparatus comprising a first data processor and a first computer readable medium; and
a control system comprising a second data processor, and a second computer readable medium, the control system communicatively coupled to the information management apparatus,
wherein the second data processor is the data processor, wherein the second computer readable medium is the computer readable medium, and
wherein executing the first set of test orders for the first plurality of samples includes executing, by the control system, the first set of test orders for the first plurality of samples received from the information management apparatus, so that the first plurality of samples are processed on one or more instruments in communication with the control system,
wherein the first computer readable medium comprises code, executable by the first data processor, to cause the first data processor to perform a method including:
  receiving, by the one or more data processors, the first set of test orders for the plurality of samples; and
  providing, by the one or more data processors, the first set of test orders to the control system;
and
wherein the second computer readable medium comprises code, executable by the second data processor, to cause the second data processor to perform a method including:
  providing, by the one or more data processors, the first plurality of test results to the information management apparatus;
  receiving, by the one or more data processors, the input data from the information management apparatus;
  after generating the one or more processing rules, receiving, by the control system from the information management apparatus, additional test orders for an additional plurality of samples; and
  after generating the one or more processing rules, receiving, by the control system from the information management apparatus, additional test orders for an additional plurality of samples; and
  after generating the one or more processing rules, executing, by the control system, the additional test orders for the additional plurality of samples, so that the additional plurality of samples are processed on the one or more instruments in communication with the control system according to the one or more generated processing rules.

14. The system of claim 12, wherein generating one or more processing rules based at least on the input data and the test results, comprises:
grouping a set of test results within the first plurality of test results; and
determining at least one threshold based upon the set of test results and the input data, based on seeing the actions taken with the test result of different patients, wherein the actions comprise the test result being either validated or being flagged for review, wherein at least one of the one or more processing rules is an autovalidation processing rule that incorporates the at least one threshold.

15. The system of claim 14, wherein the at least one threshold comprises a lower threshold and a higher threshold.

16. The system of claim 15, wherein the lower threshold and higher threshold are also defined in part by historical sample data in a patient repository.

17. The system of claim 15, wherein the system further comprises:
an output device operatively coupled to the one or more data processors, the output device configured to
  provide, by the one or more data processors, an inquiry requesting a user to confirm use of the one or more generated processing rules for sample processing;
  receive, by the one or more data processors, a selection of the one or more generated processing rules; and
  store, by the one or more data processors, the one or more generated processing rules in a data storage.

18. The system of claim 12, wherein generating one or more processing rules based at least on the input data and the test results comprises:
identifying a set of test results within the first plurality of test results, wherein the test result was measured by a same first instrument;
identifying that the test results of the set of test results have been either validated or have been flagged for additional review, wherein in the additional review a different, second instrument has been used to perform the measurement, and identifying a threshold or value range for measurement values, for which corresponding test results have been flagged for additional review, wherein at least one of the one or more processing rules is a processing rule that specifies that if a test result, measured by the first instrument, is a measurement value above the identified threshold respectively within the identified value range, then the same test is to be repeated by the second instrument.

19. One or more non-transitory computer readable media, the one or more non-transitory computer readable media comprising code, executable by one or more data processors, to implement a method comprising:

executing, by a sample processing system comprising one or more data processors, a first set of test orders for a first plurality of samples;

processing, by the sample processing system, the first plurality of samples to obtain a first plurality of test results; and generating, by the sample processing system, one or more processing rules that are used to automate decisions in a testing of samples, based at least on input data and based at least on the first plurality of test results.

20. The one or more non-transitory computer readable media of claim 19, wherein second computer readable medium code executable by a second data processor to perform the method further including:

receiving, by the sample processing system, the first plurality of test results from one or more instruments corresponding to the first plurality of test orders;

providing, by the sample processing system, the first plurality of test results to an information management apparatus; and receiving, by the sample processing system, the input data from the information management apparatus.

\* \* \* \* \*